US008507450B2

(12) United States Patent
Eckhardt et al.

(10) Patent No.: US 8,507,450 B2
(45) Date of Patent: Aug. 13, 2013

(54) CRYSTALLINE FORMS OF 1-CHLORO-4-(β-D-GLUCOPYRANOS-1-YL)-2-[4-ETHYNYL-BENZYL)-BENZENE, METHODS FOR ITS PREPARATION AND THE USE THEREOF FOR PREPARING MEDICAMENTS

(75) Inventors: Matthias Eckhardt, Biberach (DE); Frank Himmelsbach, Mittelbiberach (DE); Tanja Butz, Merklingen (DE); Martin Schuehle, Oberhoefen (DE); Hans-Juergen Martin, Biberach (DE)

(73) Assignee: Boehringer Ingelheim International GmbH, Ingelheim (DE)

( * ) Notice: Subject to any disclaimer, the term of this patent is extended or adjusted under 35 U.S.C. 154(b) by 349 days.

(21) Appl. No.: 11/470,684

(22) Filed: Sep. 7, 2006

(65) Prior Publication Data

US 2007/0054867 A1 Mar. 8, 2007

(30) Foreign Application Priority Data

Sep. 8, 2005 (EP) .................................... 05019527

(51) Int. Cl.
*A61K 31/70* (2006.01)
*C07H 5/02* (2006.01)

(52) U.S. Cl.
USPC ........................................... 514/23; 526/122

(58) Field of Classification Search
None
See application file for complete search history.

(56) References Cited

U.S. PATENT DOCUMENTS

| 4,602,023 | A | 7/1986 | Kiely et al. |
| 4,786,755 | A | 11/1988 | Kiely et al. |
| 6,414,126 | B1 | 7/2002 | Ellsworth et al. |
| 6,515,117 | B2 | 2/2003 | Ellsworth et al. |
| 6,627,611 | B2 | 9/2003 | Tomiyama et al. |
| 6,774,112 | B2 | 8/2004 | Gougoutas |
| 6,936,590 | B2 | 8/2005 | Washburn et al. |
| 7,169,761 | B2 | 1/2007 | Tomiyama et al. |
| 7,202,350 | B2 | 4/2007 | Imamura et al. |
| 7,371,732 | B2 | 5/2008 | Eickelmann et al. |
| 7,375,090 | B2 | 5/2008 | Himmelsbach et al. |
| 7,393,836 | B2 | 7/2008 | Eckhardt et al. |
| 7,417,032 | B2 | 8/2008 | Eckhardt et al. |
| 7,419,959 | B2 | 9/2008 | Eckhardt et al. |
| 7,579,449 | B2 | 8/2009 | Eckhardt et al. |
| 7,662,790 | B2 | 2/2010 | Himmelsbach et al. |
| 7,683,160 | B2 | 3/2010 | Eckhardt et al. |
| 7,687,469 | B2 | 3/2010 | Eckhardt et al. |
| 7,713,938 | B2 | 5/2010 | Himmelsbach et al. |
| 7,723,309 | B2 | 5/2010 | Himmelsbach et al. |
| 7,745,414 | B2 | 6/2010 | Eckhardt et al. |
| 7,772,191 | B2 | 8/2010 | Eckhardt et al. |
| 7,772,378 | B2 | 8/2010 | Himmelsbach et al. |
| 7,776,830 | B2 | 8/2010 | Eckhardt et al. |
| 7,847,074 | B2 | 12/2010 | Eckhardt et al. |
| 7,851,602 | B2 | 12/2010 | Himmelsbach et al. |
| 7,858,587 | B2 | 12/2010 | Eckhardt et al. |
| 7,879,806 | B2 | 2/2011 | Himmelsbach et al. |
| 7,879,807 | B2 | 2/2011 | Himmelsbach et al. |
| 8,039,441 | B2 | 10/2011 | Himmelsbach et al. |
| 2002/0137903 | A1 | 9/2002 | Ellsworth et al. |
| 2003/0064935 | A1 | 4/2003 | Gougoutas |
| 2003/0114390 | A1 | 6/2003 | Washburn et al. |
| 2004/0138148 | A1 | 7/2004 | Fushimi et al. |
| 2004/0138439 | A1 | 7/2004 | Deshpande et al. |
| 2005/0065098 | A1 | 3/2005 | Fujikura et al. |
| 2005/0124555 | A1 | 6/2005 | Tomiyama et al. |
| 2005/0187168 | A1 | 8/2005 | Eickelmann et al. |
| 2005/0209166 | A1 | 9/2005 | Eckhardt et al. |
| 2005/0233982 | A1 | 10/2005 | Himmelsbach et al. |
| 2006/0009400 | A1 | 1/2006 | Eckhardt et al. |
| 2006/0019948 | A1 | 1/2006 | Eckhardt et al. |
| 2006/0025349 | A1 | 2/2006 | Eckhardt et al. |
| 2006/0035841 | A1 | 2/2006 | Eckhardt et al. |
| 2006/0063722 | A1 | 3/2006 | Washburn et al. |
| 2006/0074031 | A1 | 4/2006 | Eckhardt et al. |
| 2006/0142210 | A1 | 6/2006 | Eckhardt et al. |
| 2006/0189548 | A1 | 8/2006 | Himmelsbach et al. |
| 2006/0234953 | A1 | 10/2006 | Himmelsbach et al. |
| 2006/0251728 | A1 | 11/2006 | Himmelsbach et al. |
| 2006/0258749 | A1 | 11/2006 | Eckhardt et al. |
| 2007/0004648 | A1 | 1/2007 | Himmelsbach et al. |
| 2007/0027092 | A1 | 2/2007 | Himmelsbach et al. |
| 2007/0049537 | A1 | 3/2007 | Eckhardt et al. |
| 2007/0054867 | A1 | 3/2007 | Eckhardt et al. |
| 2007/0073046 | A1 | 3/2007 | Eckhardt et al. |
| 2007/0249544 | A1 | 10/2007 | Himmelsbach et al. |

(Continued)

FOREIGN PATENT DOCUMENTS

| CA | 2 388 818 A1 | 4/2001 |
| CA | 2 494 177 A1 | 2/2004 |

(Continued)

OTHER PUBLICATIONS

Adachi, Tetsuya., et al; T-1095, A Renal Na+-Glucose Transporter Inhibitor, Improves Hyperglycemia in Streptozotocin-Induced Diabetic Rats; Metabolism (2000) vol. 49 No. 8 pp. 990-995.

Benhaddou, Rachida., et al; Tetra-n-Propylammonium Tetra-Oxoruthenate(VII): A Reagent of Choice for the Oxidation of Diversely Protected Glycopyranoses and Glycofuranoses to Lactones; Carbohydrate Research (1994) vol. 260 pp. 243-250.

Dohle, Wolfgang., et al; Copper-Mediated Cross-Coupling of Functionalized Arylmagnesium Reagents with Functionalized Alkyl and Benzylic Halides; Organic Letters (2001) vol. 3 No. 18 pp. 2871-2873.

Fuerstner, Alois., et al; Practical Method for the Rhodium-Catalyzed Addition of Aryl- and Alkenylboronic Acids to Aldehydes; Advanced Synthesis and Catalysis (2001) vol. 343 No. 4 pp. 343-350.

(Continued)

*Primary Examiner* — Elli Peselev

(74) *Attorney, Agent, or Firm* — Michael P. Morris; Edouard G. Lebel; David A. Dow

(57) ABSTRACT

The invention relates to a crystalline hydrate of 1-chloro-4-(β-D-glucopyranos-1-yl)-2-(4-ethynyl-benzyl)-benzene and to crystalline complexes between 1-chloro-4-(β-D-glucopyranos-1-yl)-2-(4-ethynyl-benzyl)-benzene and a natural amino acid, to methods for the preparation thereof, as well as to uses thereof for preparing medicaments.

17 Claims, 2 Drawing Sheets

U.S. PATENT DOCUMENTS

| | | | |
|---|---|---|---|
| 2007/0259821 A1 | 11/2007 | Eckhardt et al. |
| 2007/0281940 A1 | 12/2007 | Dugi et al. |
| 2008/0058379 A1 | 3/2008 | Eckhardt et al. |
| 2009/0023913 A1 | 1/2009 | Eckhardt et al. |
| 2009/0318547 A1 | 12/2009 | Eckhardt et al. |
| 2009/0326215 A1 | 12/2009 | Eckhardt et al. |
| 2010/0069310 A1 | 3/2010 | Himmelsbach et al. |
| 2010/0081625 A1 | 4/2010 | Wienrich et al. |
| 2010/0093654 A1 | 4/2010 | Himmelsbach et al. |
| 2010/0099641 A1 | 4/2010 | Himmelsbach et al. |
| 2010/0179191 A1 | 7/2010 | Himmelsbach et al. |
| 2010/0209506 A1 | 8/2010 | Eisenreich |
| 2010/0240879 A1 | 9/2010 | Eckhardt et al. |
| 2010/0249392 A1 | 9/2010 | Eckhardt et al. |
| 2010/0298243 A1 | 11/2010 | Manuchehri et al. |
| 2010/0317847 A1 | 12/2010 | Eckhardt et al. |
| 2011/0014284 A1 | 1/2011 | Eisenreich et al. |
| 2011/0046076 A1 | 2/2011 | Eickelmann et al. |
| 2011/0046087 A1 | 2/2011 | Eickelmann et al. |
| 2011/0065731 A1 | 3/2011 | Dugi et al. |
| 2011/0098240 A1 | 4/2011 | Dugi et al. |
| 2011/0178033 A1 | 7/2011 | Eckhardt et al. |
| 2011/0195917 A1 | 8/2011 | Dugi et al. |
| 2011/0236477 A1 | 9/2011 | Schneider et al. |
| 2011/0237526 A1 | 9/2011 | Weber et al. |
| 2011/0237789 A1 | 9/2011 | Weber et al. |

FOREIGN PATENT DOCUMENTS

| | | |
|---|---|---|
| CA | 2 508 024 A1 | 6/2004 |
| CA | 2 508 226 A1 | 6/2004 |
| CA | 2 557 269 A1 | 9/2005 |
| CA | 2 557 320 A1 | 9/2005 |
| CA | 2 557 801 A1 | 10/2005 |
| CA | 2 573 777 A1 | 2/2006 |
| EP | 0 206 567 A2 | 6/1986 |
| EP | 1344780 A1 | 9/2003 |
| EP | 1 385 856 A0 | 2/2004 |
| EP | 1224195 B | 5/2005 |
| EP | 1 553 094 A1 | 7/2005 |
| EP | 1 609 785 A1 | 12/2005 |
| JP | 58/164502 A | 9/1983 |
| JP | 62/030750 A | 2/1987 |
| JP | 11/124392 A | 5/1999 |
| JP | 2001/288178 A | 10/2001 |
| JP | 2003/511458 A | 3/2003 |
| JP | 2004/359630 A | 12/2004 |
| WO | 98/31697 | 7/1998 |
| WO | 01/27128 A1 | 4/2001 |
| WO | 01/74834 A1 | 10/2001 |
| WO | 02/064606 A1 | 8/2002 |
| WO | 02/083006 A2 | 10/2002 |
| WO | 03/099836 A1 | 12/2003 |
| WO | 2004/001311 A1 | 2/2004 |
| WO | 2004/052902 A1 | 6/2004 |
| WO | 2004/052903 A1 | 6/2004 |
| WO | 2004/063209 A2 | 7/2004 |
| WO | 2004/076470 A2 | 9/2004 |
| WO | 2004/080990 A1 | 9/2004 |
| WO | 2005/012326 A1 | 1/2005 |
| WO | 2005/012318 A2 | 2/2005 |
| WO | 2005/085237 A1 | 9/2005 |
| WO | 2005/085265 A1 | 9/2005 |
| WO | 2005/092877 A1 | 10/2005 |
| WO | 2006002912 A1 | 1/2006 |
| WO | 2006008038 A1 | 1/2006 |
| WO | 2006/011469 A1 | 2/2006 |
| WO | 2006010557 A1 | 2/2006 |
| WO | 2006018150 A1 | 2/2006 |
| WO | 2006/034489 A2 | 3/2006 |
| WO | 2006037537 A2 | 4/2006 |
| WO | 2006/064033 A2 | 6/2006 |
| WO | 2006/089872 A1 | 8/2006 |
| WO | 2006/108842 A1 | 10/2006 |
| WO | 2006/117360 A1 | 11/2006 |
| WO | 2006/120208 A1 | 11/2006 |
| WO | 2006117359 A1 | 11/2006 |
| WO | 2007000445 A1 | 1/2007 |
| WO | 2007/014894 A2 | 2/2007 |
| WO | 2007/025943 A2 | 3/2007 |
| WO | 2007/028814 A1 | 3/2007 |
| WO | 2007/031548 A2 | 3/2007 |

OTHER PUBLICATIONS

Hatsuda, Asanori., et al; A Practical Synthesis of Highly Functionalized Aryl Nitriles Through Cyanation of Aryl Bromides Employing Heterogeneous Pd/C; Tetrahedron Letters (2005) vol. 46 pp. 1849-1853; Elsevier Ltd.

Hutton, Craig A., et al; A Convenient Preparation of dityrosine Via Miyaura Borylation-Suzuki Coupling of Iodotyrosine Derivatives; Tetrahedron Letters (2003) vol. 44 pp. 4895-4898; Pergamon Press.

Iida, Takehiko., et al; Tributylmagnesium Ate Complex-Mediated Novel Bromine-Magnesium Exchange Reaction for Selective Monosubstitution of Dibromoarenes; Tetrahedron Letters (2001) vol. 42 pp. 4841-4844; Pergamon Press.

Jagdmann Jr, G. Erik ; Synthesis of 5-(4-Substituted Benzyl)-2,4-Diaminoquinazolines as Inhibitors of *Candida albicans* Dihydrofolate Reductase; Journal Heterocyclic Chemical (1995) vol. 32 pp. 1461-1465.

Koo, Ja Seo., et al; 2-Pyridyl Cyanate: A Useful Reagent for he Preparation of Nitriles; Synthetic Communications (1996) vol. 26 No. 20 pp. 3709-3713; Marcel Dekker, Inc.

Kuribayashi, Takeshi., et al; c-Glycosylated Aryl tins: Versatile Building Blocks for Aryl C-Glycoside Glycomimetics; J. Carbohydrate Chemistry (1999) vol. 18, No. 4 pp. 371-382.

Kuribayashi, Takeshi., et al; C-Glycosylated Diphenylmethanes and Benzophenones: The Stille Coupling Reaction of C-Glycosylated Aryl tins with Benzyl Bromides and Acid Chlorides; J. Carbohydrate Chemistry (1999) vol. 18, No. 4 pp. 393-401.

Kuribayashi, Takeshi., et al; Bis C-Glycosylated Diphenylmethanes for Stable Glycoepitope Mimetics; Syntletters (1999) vol. 6 pp. 737-740.

Langle, Sandrine., et al; Selective Double Suzuki Cross-Coupling Reactions. Synthesis of Unsymmetrical Diaryl (or Heteroaryl) Methanes; Tetrahedron Letters (2003) vol. 44 pp. 9255-9258; Pergamon Press.

McLaughlin, Mark., et al; Suzuki-Miyaura Cross-Coupling of Benzylic Phospahates with Arylboronic Acids; Organic Letters (2005) vol. 7 No. 22 pp. 4875-4878.

Neamati, Ouri., et al;, "Depsides and Depsidones as Inhibiton of HIV-1 Integrase: Dimvery of Novel Inhibitors Through 3D Database Searclung", J. Med. Chem., 1997, vol. 40, pp. 942-951.

Nobre, Sabrina M., et al; Synthesis of Diarylmethane Derivatives from Pd-Catalyzed Cross-Coupling Reactions of Benzylic Halides with Arylboronic Acids; Tetrahedron Letters (2004) vol. 45 8225-8228.

Oku, Akira., et al; T-1095, An Inhibitor or renal $Na^+$-Glucose Cotransporters, May Provide a Novel Approach to Treating Diabetes; Diabetes (1999) vol. 48 pp. 1794-1800.

Perner, Richard J., et al; 5,6,7-Trisubstituted 4-Aminopyrido[2,3-d]pyrimidines as Novel inhibitors of Adenosime Kinase; Journal of Medicinal Chemistry (2003) vol. 46 pp. 5249-5257.

Sommer, Michael Bech., et al; displacement of Halogen of 2-Halogeno-Substituted Benzonitriles with Carbonions. Preparation of (2-Cyanoaryl)arylacetonitriles; Journal of Organic Chemistry (1990) vol. 55 pp. 4817-4821.

Revesz, Lasslo., et al; SAR of Benzoylpylpyridines and Benzophenones as p38 Alpha MAP Kinase Inhibitors with Oral Activity; Bioorganic & Medicinal Chemistry Letters (2004) vol. 14 pp. 3601-3605.

Stazi, Federica., et al; Statistical Experimental Design-Driven Discovery of room-Temperature Conditions for Palladium-Catalyzed Cyanation of Aryl Bromides; Tetrahedron Letters (2005) vol. 46 1815-1818; Elsevier Ltd.

Tykwinski, Rik R; Evolution in the Palladium-Catalyzed Cross-Coupling of sp- and sp2-Hybridized Carbon Atoms; Angew Chemical International Edition (2003) vol. 42 pp. 1566-1568.

Ueta, Kiichiro., et al; Long-Term Treatment with the Na$^+$-Glucose Cotransporter Inhibitor T-1095 Causes Sustained Improvement in Hyperglycemia and Prevents Diabetic Neuropathy in Goto-Kakizaki Rats; Life Sciences (2005) vol. 76 pp. 2655-2668.

Wallace, Debra J., et al; Cyclopropylboronic Acid: Synthesis and Suzuki Cross-Coupling Reactions; Tetrahedron Letters (2002) vol. 43 pp. 6987-6990; Pergamon Press.

Xue, Song., et al; Zinc-mediated Synthesis of Alpha-C-Glycosided from 1,2-Anhydroglycosides; Synletters (2003) vol. 6 pp. 870-872.

International Search Report for PCT/EP2005/002618 mailed Jun. 30, 2005.

International Search Report for PCT/EP2006/061956 mailed on Jul. 5, 2006.

International Search report for PCT/EP2006/061957 mailed on Jul. 5, 2006.

International Search Report for PCT/EP2006/061520 mailed Jul. 26, 2006.

International Search Report for PCT/EP2006/062191 mailed Aug. 8, 2006.

International Search Report for PCT/EP2005/056806 mailed Dec. 27, 2006.

International Search Report for corresponding international application PCT/EP2006/066107 mailed Jan. 11, 2007.

International Search Report for PCT/EP2006/066347 mailed Mar. 7, 2007.

International Search Report for PCT/EP2006/065710 mailed Mar. 8, 2007.

International Search Report for PCT/EP2007/051411 mailed on May 2, 2007.

International Search Report for PCT/EP2007/054248 mailed on Jun. 18, 2007.

International Search Report for PCT/EP2006/064702 mailed on Jul. 26, 2007.

Notice of Allowance and Fee(s) Due dated Jan. 13, 2009 from U.S. Appl. No. 11/304,284, filed Dec. 15, 2005.

Non-Final Office Action dated Jun. 24, 2008 from U.S. Appl. No. 11/406,971, filed Apr. 19, 2006.

Non-Final Office Action dated Jun. 5, 2008 from U.S. Appl. No. 11/408,899, filed Apr. 21, 2006.

Non Final Office Action dated Apr. 2, 2008 from U.S. Appl. No. 11/674,839, filed Feb. 14, 2007.

Response dated Sep. 25, 2008 to Non-Final Office Action dated Apr. 2, 2008 from U.S. Appl. No. 11/674,839, filed Feb. 14, 2007.

Non-Final Office Action dated May 8, 2008 from U.S. Appl. No. 11/359,846, filed Feb. 22, 2006.

Response dated Nov. 5, 2008 to Non-Final Office Action dated May 8, 2008 from U.S. Appl. No. 11/359,846, filed Feb. 22, 2006.

Notice of Allowance and Fee(s) Due dated Feb. 3, 2009 from U.S. Appl. No. 11/359,846, filed Feb. 22, 2006.

Notice of Allowance and Fee(s) Due dated Dec. 30, 2008 from U.S. Appl. No. 11/674,839, filed Feb. 14, 2007.

Non Final Office Action dated Apr. 2, 2008 from U.S. Appl. No. 11/742,612, filed on May 1, 2007.

Response dated Sep. 25, 2008 to Non-Final Office Action dated Apr. 2, 2008 from U.S. Appl. No. 11/742,612, filed May 1, 2007.

Notice of Allowance and Fee(s) Due dated Jan. 2, 2009 from U.S. Appl. No. 11/742,612, filed May 1, 2007.

U.S. Appl. No. 13/419,784 filed Mar. 14, 2012, Inventor: Peter Eickelmann.

Figure 1: X-ray powder diffraction pattern of the crystalline complex of the compound A with proline (1:1)
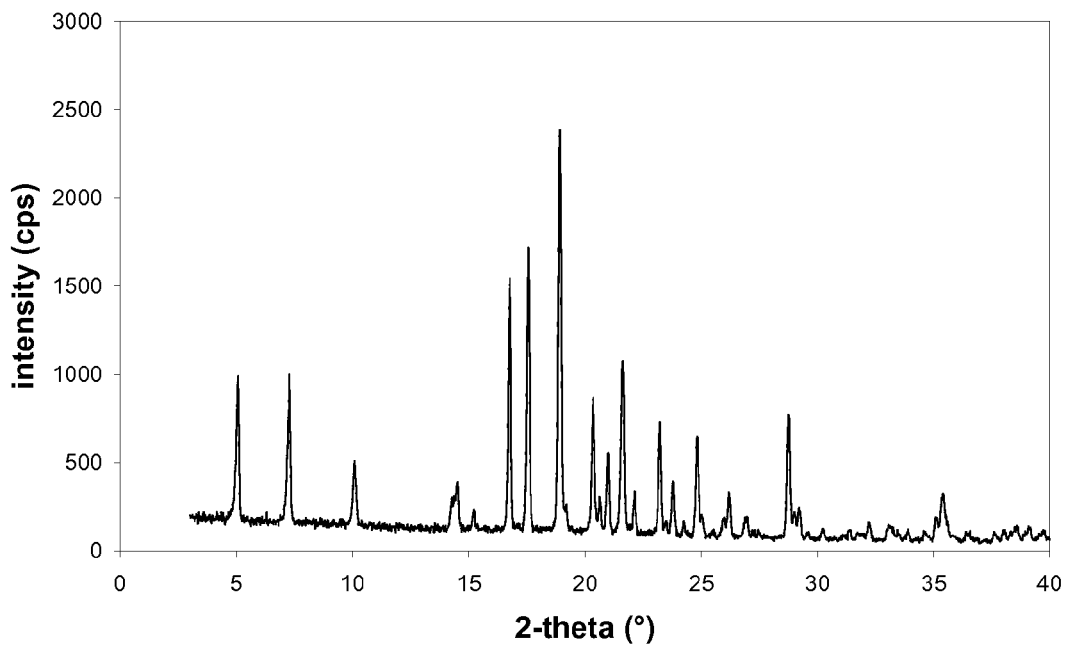
Figure 2: DSC diagram of the crystalline complex of the compound A with proline (1:1)
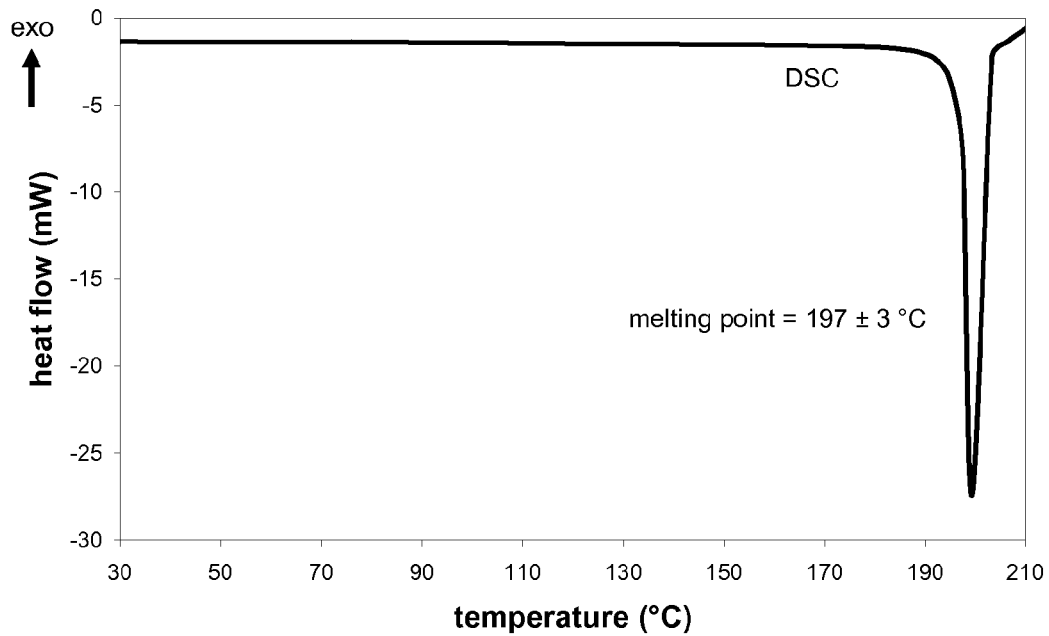

Figure 3: X-ray powder diffraction pattern of the crystalline hydrate of compound A
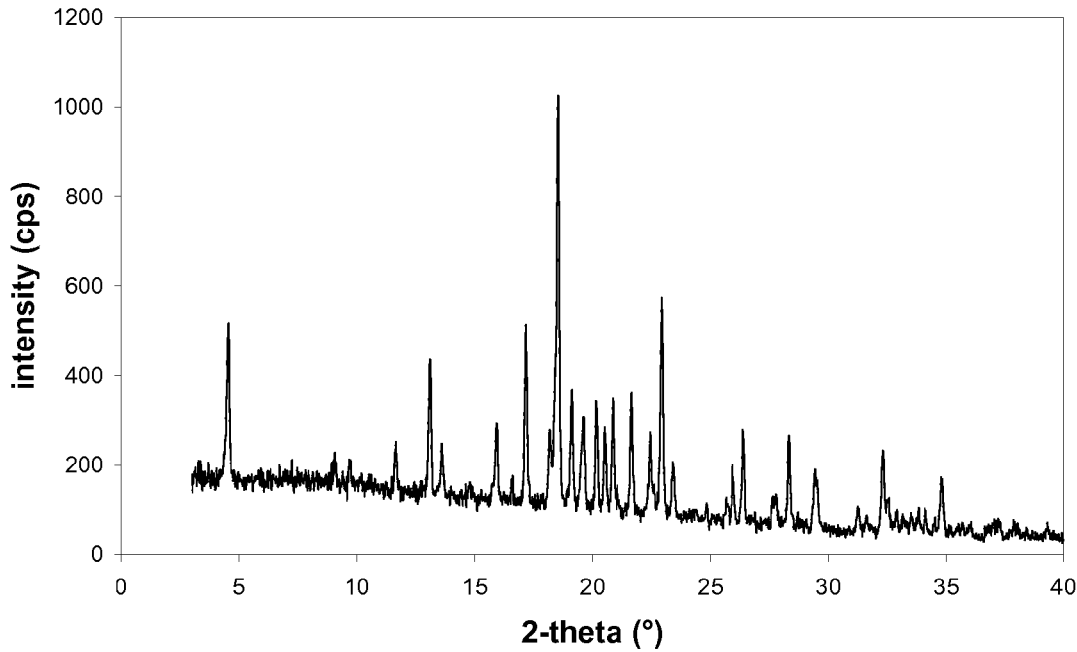
Figure 4: DSC and TG diagram of the crystalline hydrate of compound A
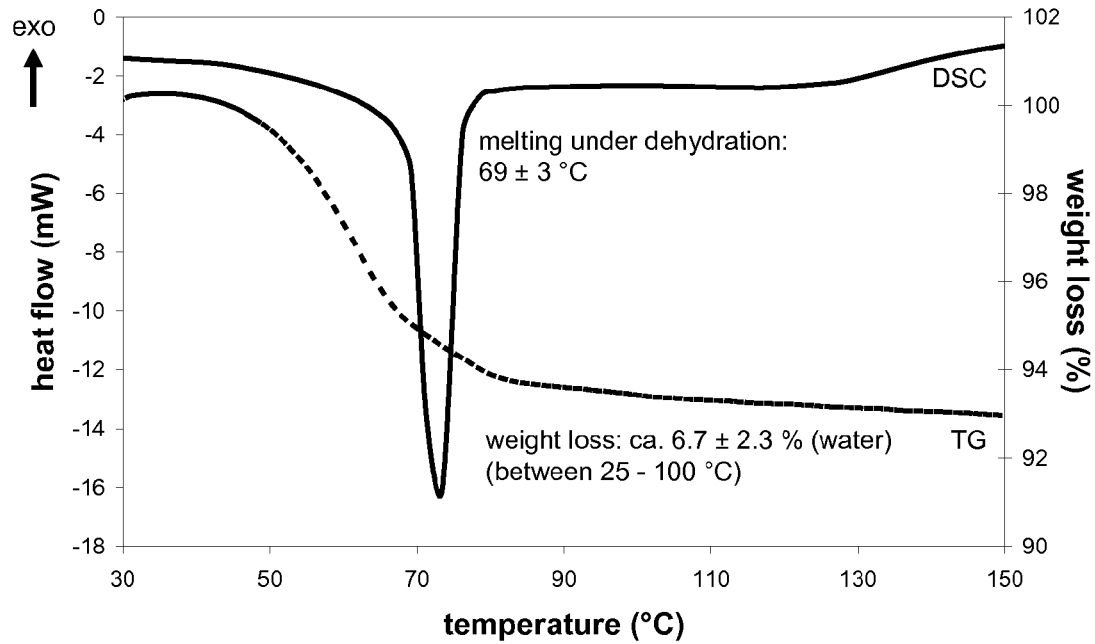

CRYSTALLINE FORMS OF 1-CHLORO-4-(β-D-GLUCOPYRANOS-1-YL)-2-[4-ETHYNYL-BENZYL)-BENZENE, METHODS FOR ITS PREPARATION AND THE USE THEREOF FOR PREPARING MEDICAMENTS

This application claims priority benefit to EP 05019527, filed Sep. 8, 2005, which is incorporated herein in its entirety.

The invention relates to a crystalline hydrate and to crystalline complexes of 1-chloro-4-(β-D-glucopyranos-1-yl)-2-(4-ethynyl-benzyl)-benzene, to methods for the preparation thereof, as well as to the use thereof for preparing medicaments.

BACKGROUND OF THE INVENTION

The compound 1-chloro-4-(β-D-glucopyranos-1-yl)-2-(4-ethynyl-benzyl)-benzene (in the following referred to it as "compound A") is described in the international patent application WO 2005/092877 and has the chemical structure according to formula A

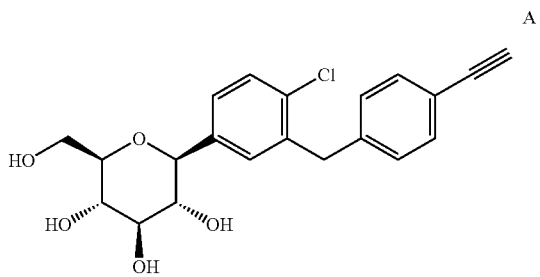 [SMILES: C#Cc1ccc(Cc2cc([C@@H]3O[C@H](CO)[C@@H](O)[C@H](O)[C@H]3O)ccc2Cl)cc1]

The compounds described therein have a valuable inhibitory effect on the sodium-dependent glucose cotransporter SGLT, particularly SGLT2. The method of manufacture of the compound A as described therein does not yield a crystalline form.

A certain pharmaceutical activity is of course the basic prerequisite to be fulfilled by a pharmaceutically active agent before same is approved as a medicament on the market. However, there are a variety of additional requirements a pharmaceutically active agent has to comply with. These requirements are based on various parameters which are connected with the nature of the active substance itself. Without being restrictive, examples of these parameters are the stability of the active agent under various environmental conditions, its stability during production of the pharmaceutical formulation and the stability of the active agent in the final medicament compositions. The pharmaceutically active substance used for preparing the pharmaceutical compositions should be as pure as possible and its stability in long-term storage must be guaranteed under various environmental conditions. This is essential to prevent the use of pharmaceutical compositions which contain, in addition to the actual active substance, breakdown products thereof, for example. In such cases the content of active substance in the medicament might be less than that specified.

Uniform distribution of the medicament in the formulation is a critical factor, particularly when the medicament has to be given in low doses. To ensure uniform distribution, the particle size of the active substance can be reduced to a suitable level, e.g. by grinding. Since breakdown of the pharmaceutically active substance as a side effect of the grinding (or micronising) has to be avoided as far as possible, in spite of the hard conditions required during the process, it is essential that the active substance should be highly stable throughout the grinding process. Only if the active substance is sufficiently stable during the grinding process it is possible to produce a homogeneous pharmaceutical formulation which always contains the specified amount of active substance in a reproducible manner.

Another problem which may arise in the grinding process for preparing the desired pharmaceutical formulation is the input of energy caused by this process and the stress on the surface of the crystals. This may in certain circumstances lead to polymorphous changes, to amorphization or to a change in the crystal lattice. Since the pharmaceutical quality of a pharmaceutical formulation requires that the active substance should always have the same crystalline morphology, the stability and properties of the crystalline active substance are subject to stringent requirements from this point of view as well.

The stability of a pharmaceutically active substance is also important in pharmaceutical compositions for determining the shelf life of the particular medicament; the shelf life is the length of time during which the medicament can be administered without any risk. High stability of a medicament in the abovementioned pharmaceutical compositions under various storage conditions is therefore an additional advantage for both the patient and the manufacturer.

The absorption of moisture reduces the content of pharmaceutically active substance as a result of the increased weight caused by the uptake of water. Pharmaceutical compositions with a tendency to absorb moisture have to be protected from moisture during storage, e.g. by the addition of suitable drying agents or by storing the drug in an environment where it is protected from moisture. Preferably, therefore, a pharmaceutically active substance should be only slightly hygroscopic.

Furthermore, the availability of a well-defined crystalline form allows the purification of the drug substance by recrystallization.

Apart from the requirements indicated above, it should be generally borne in mind that any change to the solid state of a pharmaceutical composition which is capable of improving its physical and chemical stability gives a significant advantage over less stable forms of the same medicament.

The aim of the invention is thus to provide a new, stable crystalline form of the compound A which meets important requirements imposed on pharmaceutically active substances as mentioned above.

OBJECT OF THE INVENTION

In a first aspect the present invention relates to a crystalline complex between one or more natural amino acids and 1-chloro-4-(β-D-glucopyranos-1-yl)-2-(4-ethynyl-benzyl)-benzene.

In the light of the pharmaceutical efficacy of the compound A and the advantageous physical chemical properties of the crystalline complex a second aspect of the present invention relates to a pharmaceutical composition or medicament comprising one or more crystalline complexes as defined hereinbefore and hereinafter.

In a third aspect the present invention relates to a crystalline hydrate of 1-chloro-4-(β-D-glucopyranos-1-yl)-2-(4-ethynyl-benzyl)-benzene.

In view of the pharmaceutical efficacy of the compound A a fourth aspect of the present invention relates to a pharmaceutical composition or medicament comprising one or more crystalline hydrates as defined hereinbefore and hereinafter.

In a further aspect the present invention relates to a use of one or more crystalline complexes or crystalline hydrates as defined hereinbefore or hereinafter for preparing a pharmaceutical composition which is suitable for the treatment or prevention of diseases or conditions which can be influenced by inhibiting sodium-dependent glucose cotransporter SGLT, preferably SGLT2.

In a yet further aspect the present invention relates to a use of one or more crystalline complexes or crystalline hydrates as defined hereinbefore or hereinafter for preparing a pharmaceutical composition which is suitable for the treatment or prevention of metabolic disorders.

In a further aspect the present invention relates to a use of one or more crystalline complexes or crystalline hydrates as defined hereinbefore or hereinafter for preparing a pharmaceutical composition for inhibiting the sodium-dependent glucose cotransporter SGLT2.

In a yet further aspect the present invention relates to a use of one or more crystalline complexes or crystalline hydrates as defined hereinbefore or hereinafter for preparing a pharmaceutical composition for preventing the degeneration of pancreatic beta cells and/or for improving and/or restoring the functionality of pancreatic beta cells.

In a further aspect the present invention relates to a method for making one or more crystalline complexes as defined hereinbefore and hereinafter, said method comprising the following steps:
(a) preparing a solution of 1-chloro-4-(β-D-glucopyranos-1-yl)-2-(4-ethynyl-benzyl)-benzene and the one or more natural amino acids in a solvent or a mixture of solvents;
(b) storing the solution to precipitate the crystalline complex out of solution;
(c) removing the precipitate from the solution; and
(d) drying the precipitate optionally until any excess of said solvent or mixture of solvents has been removed.

A yet further aspect of the present invention relates to a method for making one or more crystalline hydrates as defined hereinbefore and hereinafter, said method comprising the following steps:
(a) dissolving 1-chloro-4-(β-D-glucopyranos-1-yl)-2-(4-ethynyl-benzyl)-benzene in a solvent or a mixture of solvents to form a solution, preferably a nearly saturated, saturated or supersaturated solution, with the proviso that the starting material of 1-chloro-4-(β-D-glucopyranos-1-yl)-2-(4-ethynyl-benzyl)-benzene and/or said solvent or mixture of solvents contain an amount of $H_2O$ which is at least the quantity required to form a hydrate, preferably at least 1.5 mol of water per mol of 1-chloro-4-(β-D-glucopyranos-1-yl)-2-(4-ethynyl-benzyl)-benzene;
(b) storing the solution to precipitate the crystalline hydrate out of solution;
(c) removing the precipitate from the solution; and
(d) drying the precipitate optionally until any excess of said solvent or mixture of solvents has been removed.

Further aspects of the present invention become apparent to the one skilled in the art from the following detailed description of the invention and the examples.

BRIEF DESCRIPTION OF THE FIGURES

The FIG. 1 shows an X-ray powder diffractogram of the crystalline complex between the compound A and proline (1:1).

The FIG. 2 shows the determination of the melting point via DSC of the crystalline complex between the compound A and proline (1:1).

The FIG. 3 shows an X-ray powder diffractogram of the crystalline hydrate of the compound A.

The FIG. 4 shows the thermoanalysis and determination of the melting point via DSC of the crystalline hydrate of the compound A.

DETAILED DESCRIPTION OF THE INVENTION

Surprisingly, it has been found that there exist a crystalline complex between natural amino acids and the compound A. Such complexes fulfill important requirements mentioned hereinbefore. Accordingly the present invention relates to a crystalline complex between one or more natural amino acids and the compound A.

Preferably the natural amino acid is present in either its (D) or (L) enantiomeric form, most preferably as the (L) enantiomer.

Furthermore those crystalline complexes according to this invention are preferred which are formed between one natural amino acid and the compound A, most preferably between the (L) enantiomer of a natural amino acid and the compound A.

Preferred amino acids according to this invention are selected from the group consisting of phenylalanine and proline, in particular (L)-proline and (L)-phenylalanine.

According to a preferred embodiment the crystalline complex is characterized in that the natural amino acid is proline, in particular (L)-proline.

Preferably the molar ratio of the natural amino acid and the compound A is in the range from about 1:1 to 2:1; most preferably about 1:1. In the following it is referred to this embodiment as "complex (1:1)" or "1:1 complex".

Therefore a preferred crystalline complex according to this invention is a complex (1:1) between the compound A and proline; in particular of the compound A and L-proline.

Said crystalline complex of the compound A and proline may be identified and distinguished from other crystalline forms by means of their characteristic X-ray powder diffraction (XRPD) patterns.

Said crystalline complex is preferably characterised by an X-ray powder diffraction pattern that comprises peaks at 16.75, 17.55 and 18.91 degrees 2Θ (±0.05 degrees 2Θ), wherein said X-ray powder diffraction pattern is made using $CuK_{α1}$ radiation.

In particular said X-ray powder diffraction pattern comprises peaks at 5.07, 16.75, 17.55, 18.91 and 21.62 degrees 2Θ (±0.05 degrees 2Θ), wherein said X-ray powder diffraction pattern is made using $CuK_{α1}$ radiation.

More specifically said X-ray powder diffraction pattern comprises peaks at 5.07, 7.28, 16.75, 17.55, 18.91, 20.34, 21.62 and 28.75 degrees 2Θ (±0.05 degrees 2Θ), wherein said X-ray powder diffraction pattern is made using $CuK_{α1}$ radiation.

Even more specifically, the crystalline complex of the compound A and proline is characterised by an X-ray powder diffraction pattern, made using $CuK_{α1}$ radiation, which comprises peaks at degrees 2Θ (±0.05 degrees 2Θ) as contained in Table 1.

TABLE 1

X-ray powder diffraction pattern of the crystalline complex of the compound A and proline (only peaks up to 30° in 2Θ are listed):

| 2Θ [°] | d-value [Å] | Intensity I/I₀ [%] |
|---|---|---|
| 5.07 | 17.43 | 37 |
| 7.28 | 12.14 | 34 |
| 10.08 | 8.77 | 15 |
| 14.28 | 6.20 | 8 |
| 14.50 | 6.10 | 12 |

TABLE 1-continued

X-ray powder diffraction pattern of the crystalline complex of the
compound A and proline (only peaks up to 30° in 2Θ are listed):

| 2Θ [°] | d-value [Å] | Intensity I/I$_0$ [%] |
|---|---|---|
| 15.23 | 5.81 | 5 |
| 16.75 | 5.29 | 61 |
| 17.55 | 5.05 | 70 |
| 18.91 | 4.69 | 100 |
| 19.19 | 4.62 | 7 |
| 20.34 | 4.36 | 31 |
| 20.63 | 4.30 | 8 |
| 20.98 | 4.23 | 19 |
| 21.62 | 4.11 | 42 |
| 22.12 | 4.01 | 10 |
| 23.21 | 3.83 | 26 |
| 23.48 | 3.79 | 3 |
| 23.77 | 3.74 | 12 |
| 24.25 | 3.67 | 3 |
| 24.82 | 3.59 | 25 |
| 25.02 | 3.56 | 5 |
| 25.96 | 3.43 | 4 |
| 26.19 | 3.40 | 11 |
| 26.92 | 3.31 | 4 |
| 28.75 | 3.10 | 31 |
| 29.00 | 3.08 | 7 |
| 29.20 | 3.06 | 7 |
| 29.58 | 3.02 | 1 |

Even more specifically, said crystalline complex is characterised by an X-ray powder diffraction pattern, made using CuK$_{\alpha 1}$ radiation, which comprises peaks at degrees 2Θ (±0.05 degrees 2Θ) as shown in FIG. 1.

Furthermore said crystalline complex is characterised by a melting point of about 197° C.±3° C. (determined via DSC; evaluated as onset-temperature; heating rate 10 K/min). The obtained DSC curve is shown in FIG. 2. Depending on the method of manufacture and the storage of the crystalline complex a weight loss of about 1% of water can be observed by thermal gravimetry. Such a weight loss can for example result by the release of water adsorbed on the surface of said crystals.

Furthermore, it has been found that there exist a crystalline hydrate of the compound A. Accordingly the present invention relates to a crystalline hydrate of the compound A.

The crystalline hydrate of the compound A may be identified and distinguished from other crystalline forms by means of their characteristic X-ray powder diffraction (XRPD) patterns.

The crystalline hydrate is preferably characterised by an X-ray powder diffraction pattern that comprises peaks at 17.16, 18.53 and 22.94 degrees 2Θ (±0.05 degrees 2Θ), wherein said X-ray powder diffraction pattern is made using CuK$_{\alpha 1}$ radiation.

In particular said X-ray powder diffraction pattern comprises peaks at 4.53, 13.11, 17.16, 18.53 and 22.94 degrees 2Θ (±0.05 degrees 2Θ), wherein said X-ray powder diffraction pattern is made using CuK$_{\alpha 1}$ radiation.

More specifically said X-ray powder diffraction pattern comprises peaks at 4.53, 13.11, 17.16, 18.53, 19.10, 21.64 and 22.94 degrees 2Θ (±0.05 degrees 2Θ), wherein said X-ray powder diffraction pattern is made using CuK$_{\alpha 1}$ radiation.

Even more specifically, the crystalline hydrate is characterised by an X-ray powder diffraction pattern, made using CuK$_{\alpha 1}$ radiation, which comprises peaks at degrees 2Θ (±0.05 degrees 2Θ) as contained in Table 2.

TABLE 2

X-ray powder diffraction pattern of the crystalline hydrate:

| 2Θ [°] | d-value [Å] | Intensity I/I$_0$ [%] |
|---|---|---|
| 4.53 | 19.48 | 40 |
| 9.07 | 9.75 | 9 |
| 9.70 | 9.12 | 7 |
| 11.65 | 7.59 | 13 |
| 13.11 | 6.75 | 36 |
| 13.60 | 6.51 | 14 |
| 15.91 | 5.56 | 21 |
| 16.59 | 5.34 | 7 |
| 17.16 | 5.16 | 43 |
| 18.18 | 4.88 | 20 |
| 18.53 | 4.79 | 100 |
| 19.10 | 4.64 | 31 |
| 19.61 | 4.52 | 24 |
| 20.16 | 4.40 | 28 |
| 20.52 | 4.33 | 20 |
| 20.86 | 4.26 | 28 |
| 21.64 | 4.10 | 30 |
| 22.43 | 3.96 | 21 |
| 22.94 | 3.87 | 55 |
| 23.42 | 3.80 | 14 |
| 24.83 | 3.58 | 4 |
| 25.66 | 3.47 | 7 |
| 25.94 | 3.43 | 14 |
| 26.38 | 3.38 | 24 |
| 27.65 | 3.22 | 8 |
| 27.79 | 3.21 | 9 |
| 28.32 | 3.15 | 24 |
| 29.44 | 3.03 | 15 |

Even more specifically, the crystalline hydrate is characterised by an X-ray powder diffraction pattern, made using CuK$_{\alpha 1}$ radiation, which comprises peaks at degrees 2Θ (±0.05 degrees 2Θ) as shown in FIG. 3.

Furthermore the crystalline hydrate is characterised by a melting point of about 69° C.±3° C. (determined via DSC; evaluated as onset-temperature; heating rate 10 K/min). The obtained DSC curve is shown in FIG. 4.

The crystalline hydrate of the compound A is also characterised by thermal gravimetry (TG) with a weight loss of about 6.7±2.3% water up to approximately 100° C. as depicted by the dotted line in FIG. 4. The observed weight loss indicates that the crystalline hydrate represents a hydrate form with a stoichiometry in the range from about 1 to 2 mol of water per mol of the compound A.

The X-ray powder diffraction patterns are recorded, within the scope of the present invention, using a STOE-STADI P-diffractometer in transmission mode fitted with a location-sensitive detector (OED) and a Cu-anode as X-ray source (CuKα1 radiation, λ=1.5406 Å, 40 kV, 40 mA). In the Tables 1 and 2 above the values "2Θ [°]" denote the angle of diffraction in degrees and the values "d [Å]" denote the specified distances in Å between the lattice planes. The intensity shown in the FIGS. 1 and 3 is given in units of cps (counts per second).

In order to allow for experimental error, the above described 2Θ values should be considered accurate to ±0.05 degrees 2Θ. That is to say, when assessing whether a given sample of crystals of the compound A is a crystalline form in accordance with the invention, a 2Θ value which is experimentally observed for the sample should be considered identical with a characteristic value described above if it falls within ±0.05 degrees 2Θ of the characteristic value.

The melting point is determined by DSC (Differential Scanning Calorimetry) using a DSC 821 (Mettler Toledo). The weight loss is determined by thermal gravimetry (TG) using a TGA 851 (Mettler Toledo).

A further aspect of the present invention relates to a method for making the crystalline complex of the present invention as defined hereinbefore and hereinafter, said method comprising the following steps:
(a) preparing a solution of the compound A and the one or more natural amino acids in a solvent or a mixture of solvents;
(b) storing the solution to precipitate the crystalline complex out of solution;
(c) removing the precipitate from the solution; and
(d) drying the precipitate optionally until any excess of said solvent or mixture of solvents has been removed.

According to step (a) a solution of the compound A and the one or more natural amino acids in a solvent or a mixture of solvents is prepared. Preferably the solution is saturated or at least nearly saturated or even supersaturated with respect to the crystalline complex. In the step (a) the compound (A) may be dissolved in a solution comprising the one or more natural amino acids or the one or more natural amino acids may be dissolved in a solution comprising the compounds A. According to an alternative procedure the compound A is dissolved in a solvent or mixture of solvents to yield a first solution and the one or more natural amino acids are dissolved in a solvent or mixture of solvents to yield a second solution. Thereafter said first solution and said second solution are combined to form the solution according to step (a).

Preferably the molar ratio of the natural amino acid and the compound A in the solution corresponds to the molar ratio of the natural amino acid and the compound A in the crystalline complex to be obtained. Therefore a preferred molar ratio is in the range from about 1:1 to 2:1; most preferably about 1:1.

Suitable solvents are preferably selected from the group consisting of $C_{1-4}$-alkanols, water, ethylacetate, acetonitrile, acetone, diethylether, tetrahydrofuran, and mixture of two or more of these solvents.

More preferred solvents are selected from the group consisting of methanol, ethanol, isopropanol, water and mixture of two or more of these solvents, in particular mixtures of one or more of said organic solvents with water.

Particularly preferred solvents are selected from the group consisting of ethanol, isopropanol, water and mixtures of ethanol and/or isopropanol with water.

In case a mixture of water and one or more $C_{1-4}$-alkanols, in particular of methanol, ethanol and/or isopropanol, most preferably of ethanol, is taken, a preferred volume ratio of water: the alkanol is in the range from about 99:1 to 1:99; more preferably from about 50:1 to 1:80; even more preferably from about 10:1 to 1:60.

Preferably the step (a) is carried out at about room temperature (about 20° C.) or at an elevated temperature up to about the boiling point of the solvent or mixture of solvents used.

In order to reduce the solubility of the crystalline complex according to this invention in the solution, in step (a) and/or in step (b) one or more antisolvents may be added, preferably during step (a) or at the beginning of step (b). Water is an example of a suitable antisolvent. The amount of antisolvent is preferably chosen to obtain a supersaturated or saturated solution with respect to the crystalline complex.

In step (b) the solution is stored for a time sufficient to obtain a precipitate, i.e. the crystalline complex. The temperature of the solution in step (b) is about the same as or lower than in step (a). During storage the temperature of the solution is preferably lowered, preferably to a temperature in the range of 20° C. to 0° C. or even lower. The step (b) can be carried out with or without stirring. As known to the one skilled in the art by the period of time and the difference of temperature in step (b) the size, shape and quality of the obtained crystals can be controlled. Furthermore the crystallization may be induced by methods as known in the art, for example by mechanical means such as scratching or rubbing the contact surface of the reaction vessel for example with a glass rod. Optionally the (nearly) saturated or supersaturated solution may be inoculated with seed crystals.

In step (c) the solvent(s) can be removed from the precipitate by known methods as for example filtration, suction filtration, decantation or centrifugation.

In step (d) an excess of the solvent(s) is removed from the precipitate by methods known to the one skilled in the art as for example by reducing the partial pressure of the solvent(s), preferably in vacuum, and/or by heating above ca. 20° C., preferably in a temperature range below 150° C., even more preferably below 100° C.

A further aspect of the present invention relates to a method for making the crystalline hydrate of the present invention as defined hereinbefore and hereinafter, said method comprising the following steps:
(a) dissolving compound A in a solvent or a mixture of solvents to form a solution, preferably a nearly saturated, saturated or supersaturated solution, with the proviso that the starting material of compound A and/or said solvent or mixture of solvents contain an amount of $H_2O$ which is at least the quantity required to form a hydrate, preferably at least 1.5 mol of water per mol of compound A;
(b) storing the solution to precipitate the crystalline hydrate out of solution;
(c) removing the precipitate from the solution; and
(d) drying the precipitate optionally until any excess of said solvent or mixture of solvents has been removed.

According to this aspect of the invention the terms "saturated" or "nearly saturated" are related to the starting material of the compound A as used in step (a). For example a solution which is saturated with respect to the starting material of the compound A may be supersaturated with respect to its crystalline hydrate.

Suitable solvents are preferably selected from the group consisting of $C_{1-4}$-alkanols, water, ethylacetate, acetonitrile, acetone, diethylether, tetrahydrofuran, and mixture of two or more of these solvents.

More preferred solvents are selected from the group consisting of methanol, ethanol, isopropanol, water and mixture of two or more of these solvents, in particular mixtures of one or more of said organic solvents with water.

Particularly preferred solvents are selected from the group consisting of water, ethanol, isopropanol and mixtures of ethanol and/or isopropanol with water.

In case a mixture of water and one or more $C_{1-4}$-alkanols, in particular of methanol, ethanol and/or isopropanol, most preferably of ethanol, is taken, a preferred volume ratio of water: the alkanol is in the range from about 1:1 to 90:1; more preferably from about 2:1 to 10:1.

The proviso for the starting material of the compound A and/or the solvent and mixtures of solvents is that these contain an amount of $H_2O$ which is at least the quantity required to form a hydrate of the compound A; in particular at least 1 mol, preferably at least 1.5 mol of water per mol of compound A. Even more preferably the amount of water is at least 2 mol of water per mol of compound A. This means that either the compound A as starting material or said solvent or mixture of solvents, or the compound of the formula A together with said solvent or mixture of solvents contain an amount of $H_2O$ as specified above. For example if the starting material of the compound A in step (a) does contain sufficient water as specified above, a water content of the solvent(s) is not mandatory.

Preferably the step (a) is carried at about room temperature (about 20° C.) or at an elevated temperature up to about the boiling point of the solvent or mixture of solvents used.

In order to reduce the solubility of the compound A in the solution, in step (a) and/or in step (b) one or more antisolvents may be added, preferably during step (a) or at the beginning of step (b). Water is an example of a suitable antisolvent. The amount of antisolvent is preferably chosen to obtain a supersaturated or nearly supersaturated solution with respect to the crystalline hydrate.

In step (b) the solution is stored for a time sufficient to obtain a precipitate. The temperature of the solution in step (b) is about the same as or lower than in step (a). During storage the temperature of the solution containing the compound A is preferably lowered, preferably to a temperature in the range of 20° C. to 0° C. or even lower. The step (b) can be carried out with or without stirring. As known to the one skilled in the art by the period of time and the difference of temperature in step (b) the size, shape and quality of the obtained crystals can be varied. Furthermore the crystallization may be induced by methods as known in the art, for example by scratching or rubbing. Optionally the (nearly) saturated or supersaturated solution may be inoculated with seed crystals.

In step (c) the solvent(s) can be removed from the precipitate by known methods as for example filtration, suction filtration, decantation or centrifugation.

In step (d) an excess of the solvent(s) is removed from the precipitate by methods known to the one skilled in the art as for example by reducing the partial pressure of the solvent(s), preferably in vacuum, and/or by heating above ca. 20° C., preferably in a temperature range below 65° C., even more preferably below 50° C.

The compound A may be synthesized by methods as specifically and/or generally described or cited in the international application WO 2005/092877. Furthermore the biological properties of the compound A may be investigated as it is described in the international application WO 2005/092877 which in its entirety is incorporated herein by reference.

The crystalline complex and crystalline hydrate in accordance with the invention are preferably employed as drug active substances in substantially pure form, that is to say, essentially free of other crystalline forms of the compound A. Nevertheless, the invention also embraces the crystalline complex or the crystalline hydrate in admixture with another crystalline form or forms. Should the drug active substance be a mixture of crystalline forms, it is preferred that the substance comprises at least 50%-weight of the crystalline complex as described herein or at least 50%-weight of the crystalline hydrate as described herein.

In view of their ability to inhibit the SGLT activity, the crystalline complex according to the invention and the crystalline hydrate according to this invention are suitable for the preparation of pharmaceutical compositions for the treatment and/or preventative treatment of all those conditions or diseases which may be affected by the inhibition of the SGLT activity, particularly the SGLT-2 activity. Therefore, the crystalline complex according to the invention and the crystalline hydrate according to this invention are particularly suitable for the preparation of pharmaceutical compositions for prevention or treatment of diseases, particularly metabolic disorders, or conditions such as type 1 and type 2 diabetes mellitus, complications of diabetes (such as e.g. retinopathy, nephropathy or neuropathies, diabetic foot, ulcers, macroangiopathies), metabolic acidosis or ketosis, reactive hypoglycaemia, hyperinsulinaemia, glucose metabolic disorder, insulin resistance, metabolic syndrome, dyslipidaemias of different origins, atherosclerosis and related diseases, obesity, high blood pressure, chronic heart failure, oedema and hyperuricaemia. The crystalline complex according to the invention and the crystalline hydrate according to this invention are also suitable for the preparation of pharmaceutical compositions for preventing beta-cell degeneration such as e.g. apoptosis or necrosis of pancreatic beta cells. The crystalline complex according to the invention and the crystalline hydrate according to this invention are also suitable for the preparation of pharmaceutical compositions for improving or restoring the functionality of pancreatic cells, and also of increasing the number and size of pancreatic beta cells. The crystalline complex according to the invention and the crystalline hydrate according to this invention may also be used for the preparation of pharmaceutical compositions useful as diuretics or antihypertensives and suitable for the prevention and treatment of acute renal failure.

In particular, the crystalline complex according to the invention and the crystalline hydrate according to this invention are suitable for the preparation of pharmaceutical compositions for the prevention or treatment of diabetes, particularly type 1 and type 2 diabetes mellitus, and/or diabetic complications.

The dosage required to achieve the corresponding activity for treatment or prevention usually depends on the patient, the nature and gravity of the illness or condition and the method and frequency of administration and is for the patient's doctor to decide. Expediently, the dosage may be from 1 to 100 mg, preferably 1 to 30 mg, by intravenous route, and 1 to 1000 mg, preferably 1 to 100 mg, by oral route, in each case administered 1 to 4 times a day. For this purpose, the pharmaceutical compositions according to this invention preferably comprise the crystalline complex according to the invention or the crystalline hydrate according to this invention together with one or more inert conventional carriers and/or diluents. Such pharmaceutical compositions may be formulated as conventional galenic preparations such as plain or coated tablets, capsules, powders, suspensions or suppositories.

The following example of synthesis serves to illustrate a method of preparing the compound A and its crystalline complex and a crystalline hydrate. It is to be regarded only as a possible method described by way of example, without restricting the invention to its contents.

Preparation of the Starting Compounds

Example I

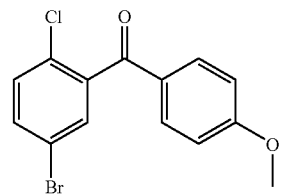 [SMILES: COc1ccc(C(=O)c2cc(Br)ccc2Cl)cc1]

(5-bromo-2-chloro-phenyl)-(4-methoxy-phenyl)-methanone 38.3 mL oxalyl chloride and 0.8 mL dimethylformamide are added to a mixture of 100 g of 5-bromo-2-chloro-benzoic acid in 500 mL dichloromethane. The reaction mixture is stirred for 14 h, then filtered and separated from all volatile constituents in the rotary evaporator. The residue is dissolved in 150 mL dichloromethane, the solution is cooled to −5° C., and 46.5 g of anisole are added. Then 51.5 g of aluminum trichloride are added batchwise so that the temperature does not exceed 5° C. The solution is stirred for another 1 h at 1-5° C. and then poured onto ice. The organic phase is separated and the aqueous phase is extracted another three times with dichloromethane. The combined organic phases are washed with aqueous 1 M hydrochloric acid, twice with 1 M sodium hydroxide solution and with brine. Then the organic phase is dried, the solvent is removed and the residue is recrystallised from ethanol.

Yield: 86.3 g (64% of theory)
Mass spectrum (ESI$^+$): m/z=325/327/329 (Br+Cl) [M+H]$^+$ Example II

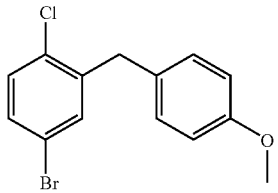 [SMILES: COc1ccc(Cc2cc(Br)ccc2Cl)cc1]

4-bromo-1-chloro-2-(4-methoxy-benzyl)-benzene

A solution of 86.2 g (5-bromo-2-chloro-phenyl)-(4-methoxy-phenyl)-methanone and 101.5 mL triethylsilane in 75 mL dichloromethane and 150 mL acetonitrile is cooled to 10° C. Then with stirring 50.8 mL of boron trifluoride etherate are added so that the temperature does not exceed 20° C. The solution is stirred for 14 h at ambient temperature, before another 9 mL triethylsilane and 4.4 mL boron trifluoride etherate are added. The solution is stirred for a further 3 h at 45-50° C. and then cooled to ambient temperature. A solution of 28 g potassium hydroxide in 70 mL water is added and the mixture is stirred for 2 h. Then the organic phase is separated and the aqueous phase is extracted three times with diisopropylether. The combined organic phases are washed twice with 2 M potassium hydroxide solution and once with brine and then dried over sodium sulfate. After the solvent has been eliminated the residue is stirred in ethanol, separated off again and dried at 60° C.

Yield: 50.0 g (61% of theory)
Mass spectrum (ESI$^+$): m/z=310/312/314 (Br+Cl) [M+H]$^+$ Example III

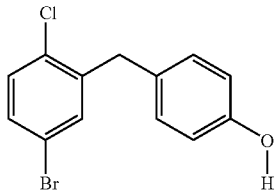 [SMILES: Oc1ccc(Cc2cc(Br)ccc2Cl)cc1]

4-(5-bromo-2-chloro-benzyl)-phenol

A solution of 14.8 g 4-bromo-1-chloro-2-(4-methoxy-benzyl)-benzene in 150 mL dichloromethane is cooled in an ice bath. Then 50 mL of a 1 M solution of boron tribromide in dichloromethane are added, and the solution is stirred for 2 h at ambient temperature. The solution is then cooled in an ice bath again, and saturated potassium carbonate solution is added dropwise. At ambient temperature the mixture is adjusted with aqueous 1 M hydrochloric acid to a pH of 1, the organic phase is separated and the aqueous phase is extracted another three times with ethyl acetate. The combined organic phases are dried over sodium sulfate and the solvent is removed completely.

Yield: 13.9 g (98% of theory)
Mass spectrum (ESI$^-$): m/z=295/297/299 (Br+Cl) [M−H]$^-$ Example IV

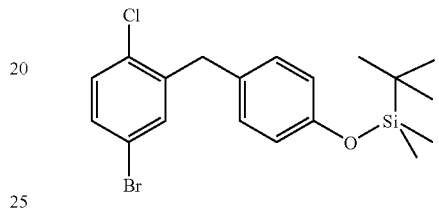

[4-(5-bromo-2-chloro-benzyl)-phenoxy]-tert-butyl-dimethyl-silane

A solution of 13.9 g 4-(5-bromo-2-chloro-benzyl)-phenol in 140 mL dichloromethane is cooled in an ice bath. Then 7.54 g tert-butyldimethylsilylchlorid in 20 mL dichloromethane are added followed by 9.8 mL triethylamine and 0.5 g dimethylaminopyridine. The solution is stirred for 16 h at ambient temperature and then diluted with 100 mL dichloromethane. The organic phase is washed twice with aqueous 1 M hydrochloric acid and once with aqueous sodium hydrogen carbonate solution and then dried over sodium sulfate. After the solvent has been removed the residue is filtered through silica gel (cyclohexane/ethyl acetate 100:1).

Yield: 16.8 g (87% of theory)
Mass spectrum (EI): m/z=410/412/414 (Br+Cl) [M]$^+$ Example V

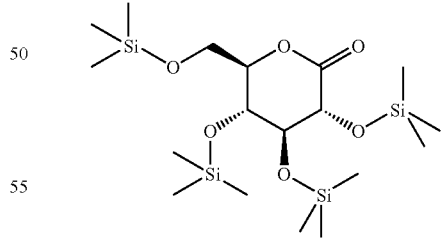

2,3,4,6-tetrakis-O-(trimethylsilyl)-D-glucopyranone

A solution of 20 g D-glucono-1,5-lactone and 98.5 mL N-methylmorpholine in 200 mL of tetrahydrofuran is cooled to −5° C. Then 85 mL trimethylsilylchloride are added dropwise so that the temperature does not exceed 5° C. The solution is then stirred for 1 h at ambient temperature, 5 h at 35° C. and again for 14 h at ambient temperature. After the addition of 300 mL toluene the solution is cooled in the ice bath, and 500 mL water are added so that the temperature does not exceed 10° C. The organic phase is then separated and washed in each case once with aqueous sodium dihydrogen phosphate solution, water and brine. The solvent is removed and the residue is azeotropically dried with toluene.

Yield: 52.5 g (approx. 90% pure)

Mass spectrum (ESI$^+$): m/z=467 [M+H]$^+$

Example VI

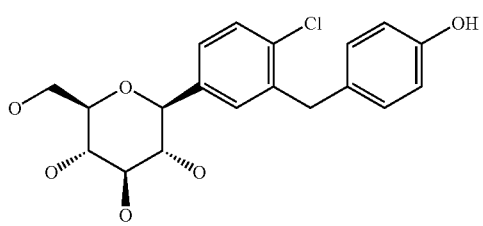 [SMILES: OC[C@H]1O[C@@H](c2ccc(Cl)c(Cc3ccc(O)cc3)c2)[C@H](O)[C@@H](O)[C@@H]1O]

1-chloro-4-(β-D-glucopyranos-1-yl)-2-(4-hydroxy-benzyl)-benzene

A solution of 4.0 g [4-(5-bromo-2-chloro-benzyl)-phenoxy]-tert-butyl-dimethyl-silane in 42 mL dry diethyl ether is cooled to −80° C. under argon. 11.6 mL of a 1.7 M solution of tert-butyllithium in pentane are slowly added dropwise to the cooled solution, and then the solution is stirred for 30 min at −80° C. This solution is then added dropwise through a transfer needle, which is cooled with dry ice, to a solution of 4.78 g 2,3,4,6-tetrakis-O-(trimethylsilyl)-D-glucopyranone in 38 mL diethyl ether chilled to −80° C. The resulting solution is stirred for 3 h at −78° C. Then a solution of 1.1 mL methanesulfonic acid in 35 mL methanol is added and the solution is stirred for 16 h at ambient temperature. The solution is then neutralized with solid sodium hydrogen carbonate, ethyl acetate is added and the methanol is removed together with the ether. Aqueous sodium hydrogen carbonate solution is added to the remaining solution that is extracted then four times with ethyl acetate. The organic phases are dried over sodium sulfate and evaporated down. The residue is dissolved in 30 mL acetonitrile and 30 mL dichloromethane and the solution is cooled to −10° C. After the addition of 4.4 mL triethylsilane 2.6 mL boron trifluoride etherate are added dropwise so that the temperature does not exceed −5° C. After the addition the solution is stirred for another 5 h at −5 to −10° C. and then quenched by the addition of aqueous sodium hydrogen carbonate solution. The organic phase is separated off and the aqueous phase is extracted four times with ethyl acetate. The combined organic phase are dried over sodium sulfate, the solvent is removed and the residue is purified using silica gel. The product then obtained is an approx. 6:1 mixture of β/α which can be converted into the pure β-anomer by global acetylation of the hydroxy groups with acetic anhydride and pyridine in dichloromethane and recrystallizing the product from ethanol. The product thus obtained is converted into the title compound by reacting in methanol with 4 M potassium hydroxide solution.

Yield: 1.6 g (46% of theory)

Mass spectrum (ESI$^+$): m/z=398/400 (Cl) [M+H]$^+$

Example VII

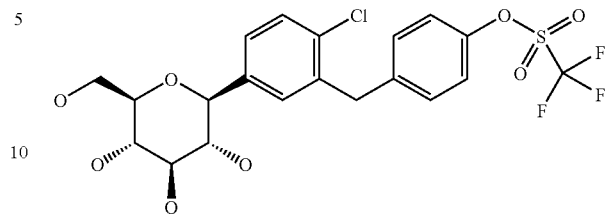

1-chloro-4-(β-D-glucopyranos-1-yl)-2-[4-(trifluoromethylsulphonyloxy)-benzyl]-benzene 10 mg 4-dimethylaminopyridine are added to a solution of 0.38 g 1-chloro-4-(β-D-glucopyranos-1-yl)-2-(4-hydroxy-benzyl)-benzene, 0.21 mL triethylamine and 0.39 g N,N-bis-(trifluoromethanesulfonyl)-aniline in 10 mL dry dichloromethane. The solution is stirred for 4 h at ambient temperature and then combined with brine. The resultant solution is extracted with ethyl acetate, the organic extracts are dried over sodium sulfate, and the solvent is removed. The residue is chromatographed through silica gel (dichloromethane/methanol 1:0->4:1).

Yield: 0.33 g (64% of theory)

Mass spectrum (ESI$^+$): m/z=530/532 (Cl) [M+NH$_4$]$^+$

Preparation of the Compound A:

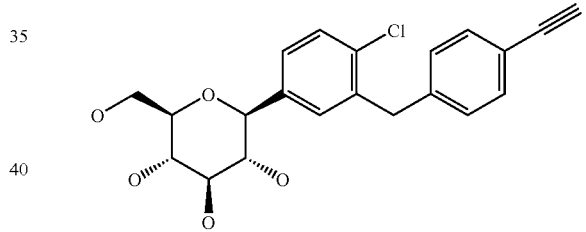

1-chloro-4-(β-D-glucopyranos-1-yl)-2-(4-ethynyl-benzyl)-benzene 25 mg of copper iodide, 44 mg of bis-(triphenylphosphine)-palladium dichloride, 0.30 mL triethylamine and finally 0.14 mL of trimethylsilylacetylene are added under argon to a solution of 0.32 g 1-chloro-4-(β-D-glucopyranos-1-yl)-2-[4-(trifluoromethylsulphonyloxy)-benzyl]-benzene in 3 mL of dimethylformamide. The flask is tightly sealed and stirred for 8 h at 90° C. Then another 25 mg of bis-(triphenylphosphine)-palladium dichloride and 0.1 mL trimethylsilylacetylene are added, and the solution is stirred for a further 10 h at 90° C. Then aqueous sodium hydrogen carbonate solution is added, the resultant mixture is extracted three times with ethyl acetate, and the combined organic phases are dried over sodium sulfate. After the solvent has been eliminated the residue is dissolved in 5 mL of methanol and combined with 0.12 g potassium carbonate. The mixture is stirred for 1 h at ambient temperature and then neutralized with 1 M hydrochloric acid. Then the methanol is evaporated off, the residue is combined with brine and extracted with ethyl acetate. The organic extracts collected are dried over sodium sulfate, and the solvent is removed. The residue is chromatographed through silica gel (dichloromethane/methanol 1:0->5:1).

Yield: 0.095 g (40% of theory)

Mass spectrum (ESI+): m/z=406/408 (Cl) [M+NH$_4$]+

Preparation of the Crystalline Complex (1:1) with Proline:

156 mg 1-chloro-4-(β-D-glucopyranos-1-yl)-2-(4-ethynyl-benzyl)-benzene (obtained as described above) and 46 mg L-proline are dissolved in 0.72 mL water/ethanol mixture (1:30 volume ratio) upon heating to about 60° C. The solution is allowed to cool to about 20° C. within 4 to 5 h. After about 16 h the crystalline complex is isolated as white crystals by filtration. If necessary the crystallisation may be initiated by scratching with a glass rod or metal spatula for example or by inoculating with seed crystals. Residual solvent is removed by storing the crystals at elevated temperature (50 to 60° C.) for about 4 h to yield 119 mg of the crystalline 1:1 complex between L-proline and 1-chloro-4-(β-D-glucopyranos-1-yl)-2-(4-ethynyl-benzyl)-benzene.

The obtained crystalline complex is characterized by a X-ray powder diffraction pattern as contained in Table 1 and as depicted in FIG. 1. Furthermore the resulting crystalline complex is characterized by a melting point of 197° C.±3° C.

Preparation of the Crystalline Hydrate:

Variant 1:

200 mg 1-chloro-4-(β-D-glucopyranos-1-yl)-2-(4-ethynyl-benzyl)-benzene (obtained as described above) are dissolved in 10 ml water with heating to about 60° C. The resultant solution is allowed to cool to about 20° C. and stored for about 18 h. If necessary crystallisation may be initiated by scratching with a glass rod or metal spatula for example or by inoculating using seed crystals. The crystals are isolated by methods well-known.

Variant 2:

200 mg 1-chloro-4-(β-D-glucopyranos-1-yl)-2-(4-ethynyl-benzyl)-benzene (obtained as described above) are dissolved in 2 mL ethanol and the resulting solution is added dropwise with stirring to 10 mL water at about 20° C. After the addition of a seed crystal (obtained as described above) the resulting solution is stored at about 20° C. Crystallisation may also be initiated by scratching with a glass rod or metal spatula for example. After 16 h the crystalline precipitate is isolated by filtration. Residual solvent is removed by storing the crystals at slightly elevated temperature (40 to 50° C.) in vacuo for about 4 h.

The obtained crystalline hydrate is characterized by a X-ray powder diffraction pattern as contained in Table 2 and as depicted in FIG. 3. Furthermore the resulting crystalline complex is characterized by a melting point of 69° C.±3° C.

The invention claimed is:

1. A crystalline complex of 1-chloro-4-(β-D-glucopyranos-1-yl)-2-(4-ethynyl-benzyl)-benzene and proline, wherein said complex has an X-ray powder diffraction pattern that comprises peaks at 5.07, 7.28, 16.75, 17.55, 18.91, 20.34, 21.62, 23.21, and 28.75 degrees 2Θ (±0.05 degrees 2Θ), wherein said X-ray powder diffraction pattern is made using CuK$_{α1}$ radiation.

2. A crystalline complex according to claim 1 wherein said complex is of 1-chloro-4-(β-D-glucopyranos-1-yl)-2-(4-ethynyl-benzyl)-benzene and proline with a molar ratio of about 1:1.

3. A pharmaceutical composition comprising the crystalline complex in accordance with claim 1.

4. A crystalline hydrate of 1-chloro-4-(β-D-glucopyranos-1-yl)-2-(4-ethynyl-benzyl)-benzene, said crystalline hydrate having an X-ray powder diffraction pattern that comprises peaks at 4.53, 13.11, 17.16, 18.53, 19.10, 20.16, 20.86, 21.64 and 22.94 degrees 2Θ (±0.05 degrees 2Θ), wherein said X-ray powder diffraction pattern is made using CuK$_{α1}$ radiation.

5. A crystalline hydrate according to claim 4 characterized by a content of water in the range from about 1 to 2 mol per mol of 1-chloro-4-(β-D-glucopyranos-1-yl)-2-(4-ethynyl-benzyl)-benzene.

6. A crystalline hydrate of 1-chloro-4-(β-D-glucopyranos-1-yl)-2-(4-ethynyl-benzyl)-benzene wherein at least 50% of said substance is present in the form of a crystalline hydrate in accordance with claim 4.

7. A pharmaceutical composition comprising a crystalline hydrate according to claim 4.

8. A method of treating metabolic disorders, said method comprised of the step of administering to a patient in need thereof a therapeutically effective amount of a crystalline complex according to claim 1 or a pharmaceutically acceptable salt thereof.

9. The method of claim 8 wherein said metabolic disorder is selected from the group consisting of type 1 and type 2 diabetes mellitus, complications of diabetes, metabolic acidosis or ketosis, reactive hypoglycaemia, hyperinsulinaemia, glucose metabolic disorder, insulin resistance, metabolic syndrome, dyslipidaemias of different origins, atherosclerosis and related diseases, obesity, high blood pressure, chronic heart failure, oedema and hyperuricaemia.

10. A method of treating metabolic disorders said method comprised of the step of administering to a patient in need thereof a therapeutically effective amount of a compound according to claim 4 or a pharmaceutically acceptable salt thereof.

11. The method of claim 10 wherein said metabolic disorder is selected from the group consisting of type 1 and type 2 diabetes mellitus, complications of diabetes, metabolic acidosis or ketosis, reactive hypoglycaemia, hyperinsulinaemia, glucose metabolic disorder, insulin resistance, metabolic syndrome, dyslipidaemias of different origins, atherosclerosis and related diseases, obesity, high blood pressure, chronic heart failure, oedema and hyperuricaemia.

12. A method of inhibiting the sodium dependent glucose cotransporter SGLT2 said method comprised of administering to a patient in need thereof a therapeutically effective amount of a crystalline complex according to claim 1 or a pharmaceutically acceptable salt thereof.

13. A method of inhibiting the sodium dependent glucose cotransporter SGLT2 said method comprised of administering to a patient in need thereof a therapeutically effective amount of a crystalline complex according to claim 4 or a pharmaceutically acceptable salt thereof.

14. A method of treating the degeneration of pancreatic beta cells and/or for improving and/or restoring the functionality of pancreatic beta cells, said method comprised of the step of administering to a patient in need thereof a therapeutically effective amount of a crystalling complex according to claim 1 or a pharmaceutically acceptable salt thereof.

15. A method of treating the degeneration of pancreatic beta cells and/or for improving and/or restoring the functionality of pancreatic beta cells said method comprised of the step of administering to a patient in need thereof a therapeutically effective amount of a crystalline complex according to claim 4 or a pharmaceutically acceptable salt thereof.

16. A method of making the crystalline complex in accordance with claim 1, said method comprising the following steps:
(a) preparing a solution of 1-chloro-4-(β-D-glucopyranos-1-yl)-2-(4-ethynyl-benzyl)-benzene and proline in a solvent or a mixture of solvents;

(b) storing the solution to precipitate the crystalline complex out of solution;
(c) removing the precipitate from the solution; and
(d) drying the precipitate until any excess of said solvent or mixture of solvents has been removed.

17. A method for making the crystalline hydrate in accordance with claim 4, said method comprising the following steps:
(a) dissolving 1-chloro-4-(β-D-glucopyranos-1-yl)-2-(4-ethynyl-benzyl)-benzene in a solvent or a mixture of solvents to form a solution, with the proviso that the starting material of 1-chloro-4-(β-D-glucopyranos-1-yl)-2-(4-ethynyl-benzyl)-benzene and/or said solvent or mixture of solvents contain an amount of $H_2O$ which is at least the quantity required to form a hydrate;
(b) storing the solution to precipitate the crystalline hydrate out of solution;
(c) removing the precipitate from the solution; and
(d) drying the precipitate until any excess of said solvent or mixture of solvents has been removed.

* * * * *